(12) United States Patent
Shioda

(10) Patent No.: US 9,207,445 B2
(45) Date of Patent: Dec. 8, 2015

(54) MEDICAL THREE-DIMENSIONAL OBSERVATION APPARATUS

(71) Applicant: OLYMPUS CORPORATION, Tokyo (JP)

(72) Inventor: Keiji Shioda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/556,513

(22) Filed: Dec. 1, 2014

(65) Prior Publication Data

US 2015/0085081 A1   Mar. 26, 2015

Related U.S. Application Data

(63) Continuation of application No. PCT/JP2013/063705, filed on May 16, 2013.

(30) Foreign Application Priority Data

May 30, 2012   (JP) ................. 2012-123726

(51) Int. Cl.
| | |
|---|---|
| *G02B 21/36* | (2006.01) |
| *H04N 13/02* | (2006.01) |
| *H04N 13/00* | (2006.01) |
| *A61B 1/00* | (2006.01) |
| *G02B 21/22* | (2006.01) |

(52) U.S. Cl.
CPC .......... *G02B 21/367* (2013.01); *A61B 1/00193* (2013.01); *G02B 21/22* (2013.01); *G02B 21/365* (2013.01); *G02B 21/368* (2013.01); *H04N 13/004* (2013.01); *H04N 13/007* (2013.01); *H04N 13/0239* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,935,810 | A * | 6/1990 | Nonami et al. ................. | 348/45 |
| 6,364,888 | B1 * | 4/2002 | Niemeyer et al. ............. | 606/130 |
| 6,493,608 | B1 * | 12/2002 | Niemeyer ..................... | 700/302 |

(Continued)

FOREIGN PATENT DOCUMENTS

| | | |
|---|---|---|
| JP | A-2003-167924 | 6/2003 |
| JP | A-2003-203241 | 7/2003 |

(Continued)

OTHER PUBLICATIONS

International Search Report issued in International Patent Application No. PCT/JP2013/063705 dated Aug. 20, 2013 (with translation).

(Continued)

*Primary Examiner* — Christopher S Kelley
*Assistant Examiner* — Asmamaw G Tarko
(74) *Attorney, Agent, or Firm* — Oliff PLC

(57) ABSTRACT

A medical three-dimensional observation apparatus includes at least a pair of imaging units, a three-dimensional image processing unit, a calculating unit, and an index superimposing unit. The imaging units image a .specimen from different viewpoints. The three-dimensional image processing unit displays a three-dimensional image of the specimen on a display in accordance with images of the specimen. The calculating unit calculates a region of a three-dimensional reproduction space of the display in which the three-dimensional image of the specimen is to be reproduced. The index superimposing unit superimposes an annotation image on a depth position corresponding to the region in which the three-dimensional image is reproduced.

1 Claim, 5 Drawing Sheets

(56) References Cited

U.S. PATENT DOCUMENTS

| | | |
|---|---|---|
| 8,537,209 B2 | 9/2013 | Iwasaki et al. |
| 2013/0093763 A1 | 4/2013 | Shinoda et al. |
| 2014/0055745 A1* | 2/2014 | Sato et al. ............ 351/206 |

FOREIGN PATENT DOCUMENTS

| JP | A-2006-218233 | 8/2006 |
|---|---|---|
| JP | A-2009-168499 | 7/2009 |
| JP | A-2013-9864 | 1/2013 |
| JP | A-2013-101599 | 5/2013 |

OTHER PUBLICATIONS

Office Action issued in Japanese Patent Application No. 2013-556930 dated Jun. 3, 2014 (with translation).

Dec. 11, 2014 International Preliminary Report on Patentability issued in International Application No. PCT/JP2013/063705.

* cited by examiner

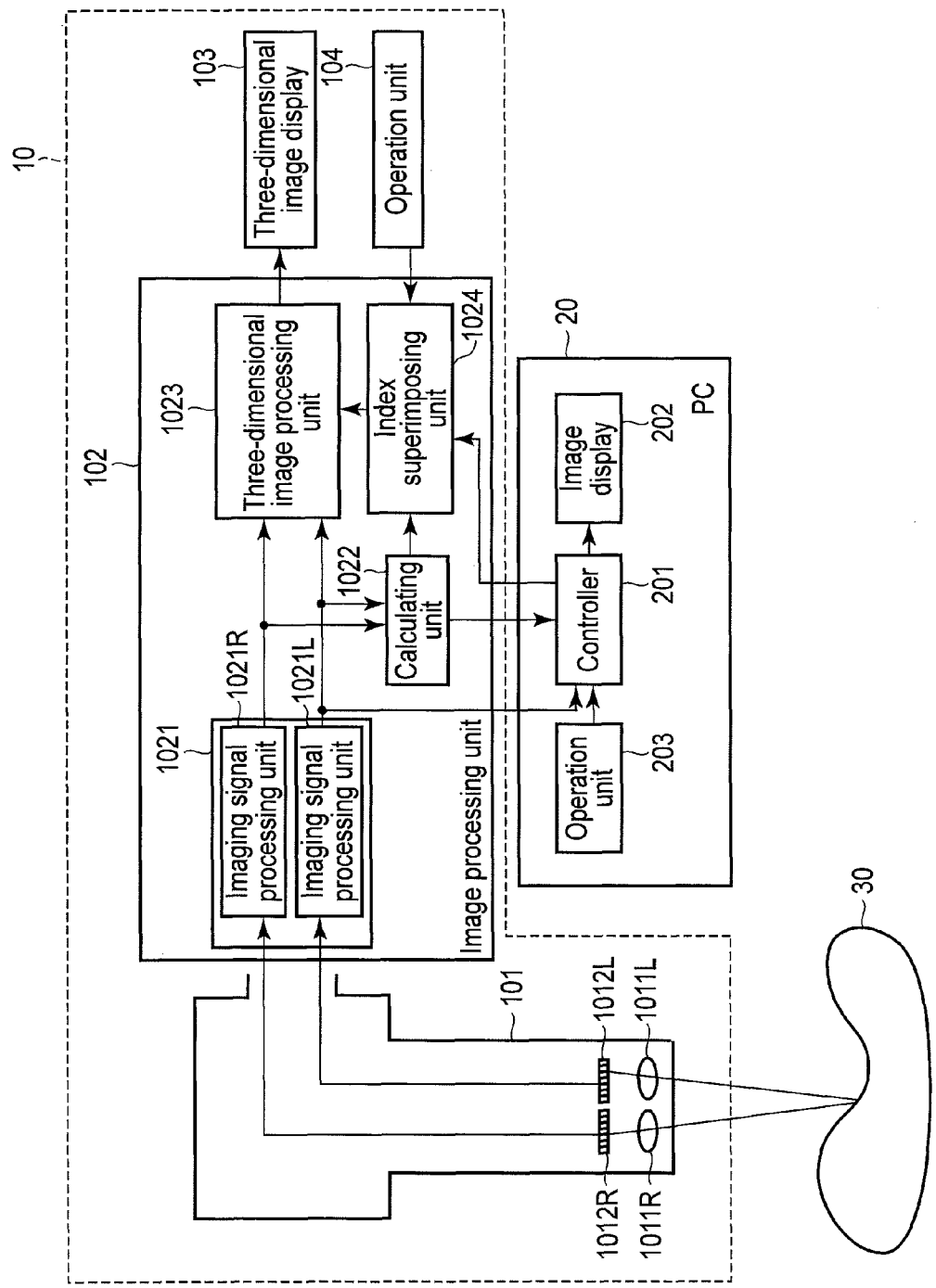
F I G. 1

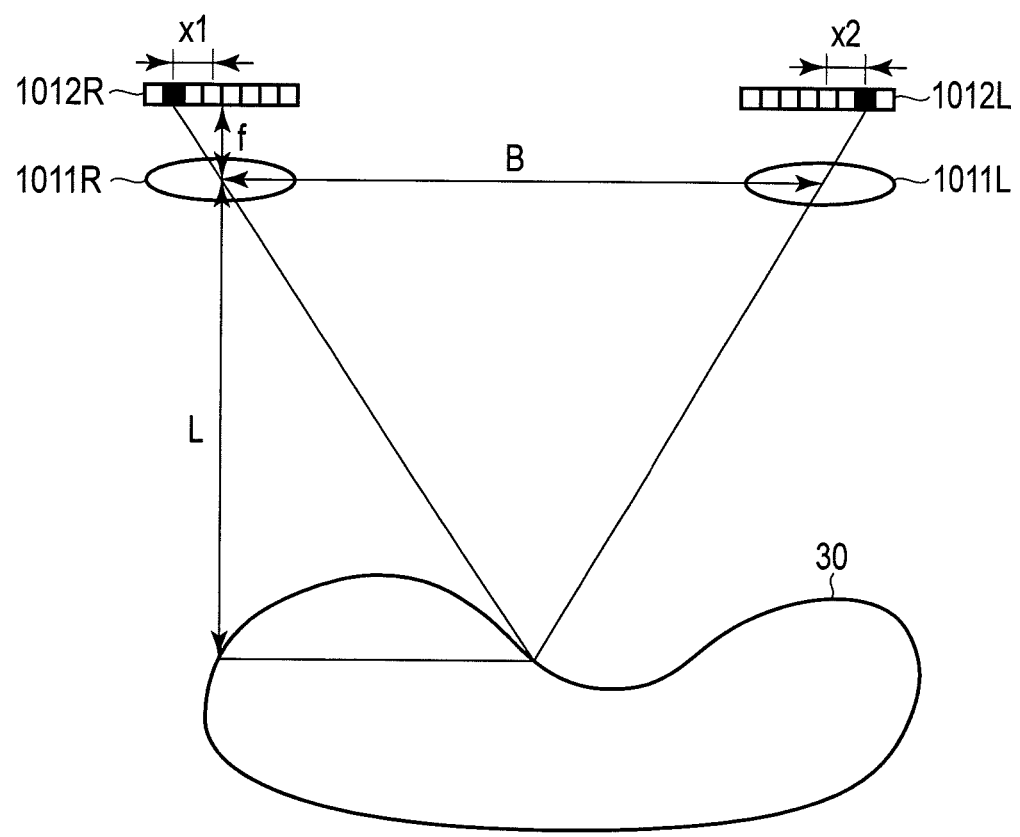
F I G. 2

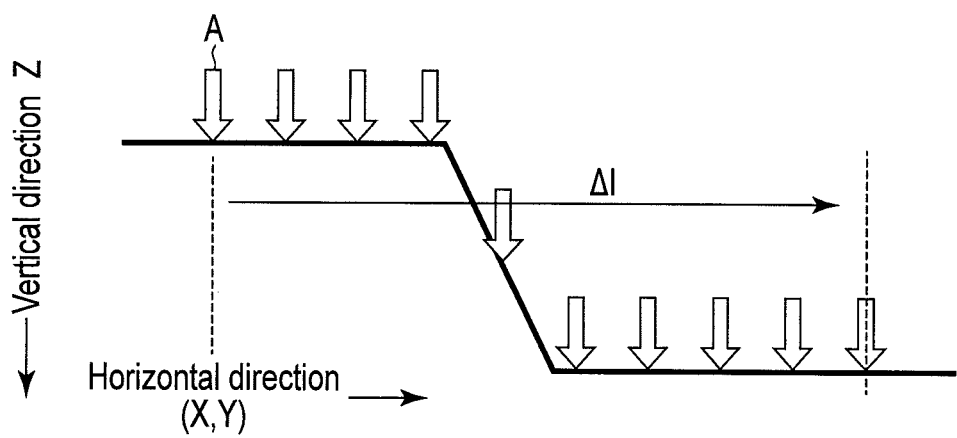
F I G. 7
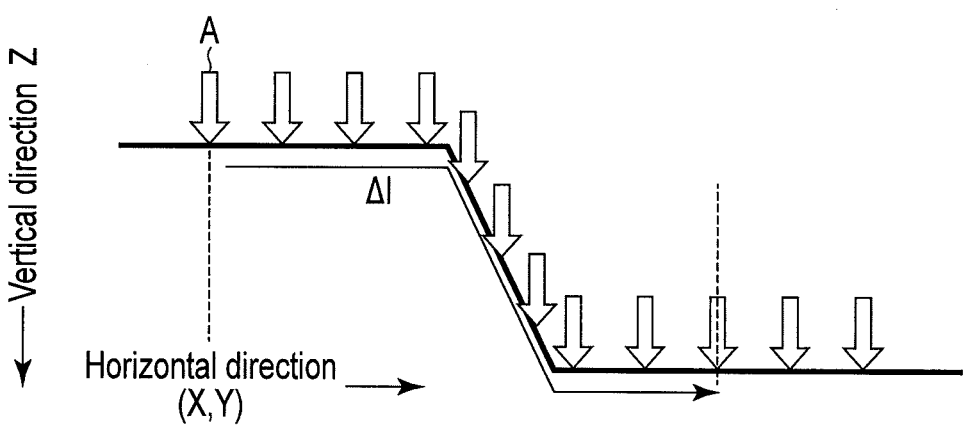
F I G. 8

MEDICAL THREE-DIMENSIONAL OBSERVATION APPARATUS

CROSS-REFERENCE TO RELATED APPLICATIONS

This application is a Continuation Application of PCT Application No. PCT/JP2013/063705, filed May 16, 2013 and based upon and claiming the benefit of priority from the prior Japanese Patent Application No. 2012-123726, filed May 30, 2012, the entire contents of both of which are incorporated herein by reference.

BACKGROUND OF THE INVENTION

1. Field of the Invention

The present invention relates to a medical three-dimensional observation apparatus which enables an image of a specimen to be observed as a three-dimensional image. 2. Description of the Related Art Recently, there have been known microscopes and endoscopes for use in, for example, surgery that enable the observation of a three-dimensional image of the inside of the body cavity of a specimen. These microscopes and endoscopes (hereinafter referred to as medical three-dimensional observation apparatuses) that enable observation of three-dimensional images make it possible to recognize the three-dimensional structure of the specimen, and are therefore used in various situations. Particularly in educational facilities, an experienced doctor may guide students or trainee doctors by showing them a particular part of an image of the inside of a body cavity obtained by an electronic microscope. For such guidance, the part is more clearly shown when specified in a three-dimensional image than in a two-dimensional image. In relation to this technique, there has been also known a technique for adding annotations such as arrows and comments to a position specified in an image (e.g., Jpn. Pat. Appln. KOKAI Publication No. 2006-218233).

BRIEF SUMMARY OF THE INVENTION

According to an aspect of the invention, a medical three-dimensional observation apparatus comprising: an imaging unit comprising a first imaging system and a second imaging system for an observation of a three-dimensional image, the first imaging system including a first observation window and generating a left image signal, and the second imaging system including a second observation window and generating a right image signal; an instruction unit operated by an observer, configured to issue an instruction to move an annotation image for the three-dimensional image as a two-dimensional position information; a calculating unit configured to calculate a depth position of the annotation image for the three-dimensional image corresponding to a position indicated by the two-dimensional position information on the basis of a distance between an optical axis of the first imaging system and an optical axis of the second imaging system; a three-dimensional image processing unit configured to generate a left image and a right image for the observation of a three-dimensional image on the basis of the left image signal and the right image signal; an index superimposing unit configured to calculate a display position of the annotation image for the three-dimensional image on the basis of the depth position calculated by the calculating unit and the two-dimensional position information issued by the instruction unit, and to superimpose the annotation image on each of the left image and the right image on the basis of the display position; and a display configured to display the left image and the right image superimposed the annotation image so that the observation of the three-dimensional image is able to be performed, wherein the index superimposing unit compares a distance corresponding to the depth position with a distance corresponding to a periphery of the position indicated by the two-dimensional position information, so that the display position of the annotation image is always located before an image of a specimen in the left image and the right image, and superimposes the annotation image on each of the left image and the right image to avoid the image of a specimen if the image of the specimen is located closer to the periphery of the annotation image than the annotation image.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram showing the configuration of a medical three-dimensional observation apparatus according to an embodiment of the present invention;

FIG. 2 is a diagram illustrating the principle of a triangular ranging method using binocular imaging systems;

FIG. 7 is a diagram showing the change of the movement amount $\Delta l$ on a three-dimensional image when the relation between the operation amount $\Delta M$ and the movement amount $\Delta l$ is determined without considering the change of depth; and FIG. 8 is a diagram showing the change of the movement amount $\Delta l$ on a three-dimensional image when the relation between the operation amount $\Delta M$ and the movement amount $\Delta l$ is determined considering the change of depth.

DETAILED DESCRIPTION OF THE INVENTION

Figure 3:
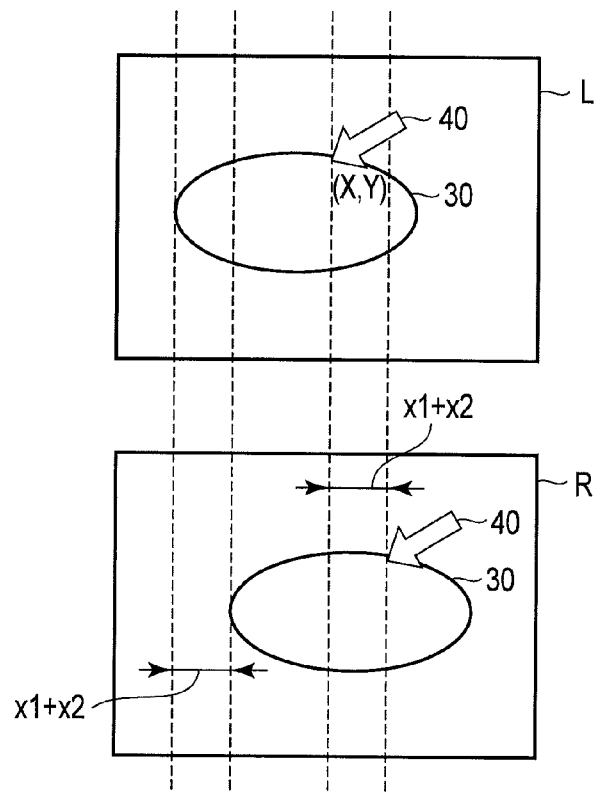
FIG. 3 is a diagram illustrating the superimposition of a virtual arrow image.

Hereinafter, an embodiment of the present invention will be described with reference to the drawings.

FIG. 1 is a diagram showing the configuration of a medical three-dimensional observation apparatus according to an embodiment of the present invention. FIG. 1 shows an example of how the medical three-dimensional observation apparatus is applied to an electronic image microscope. The technique according to the present embodiment is applicable to various medical observation apparatuses which enable the observation of a three-dimensional image. For example, the technique according to the present embodiment is also applicable to an electron microscope capable of three-dimensional observation.

A medical three-dimensional observation apparatus 10 shown in FIG. 1 roughly includes an imaging unit 101, an image processing unit 102, a three-dimensional image display 103, and an operation unit 104. The medical three-dimensional observation apparatus 10 can be connected to a personal computer (hereinafter referred to as a PC) 20 to be able to communicate with each other.

The imaging unit 101 has binocular imaging systems to image a specimen 30 from different viewpoints. The imaging unit 101 in FIG. 1 has imaging systems configured to have a horizontal parallax. In other words, each imaging system includes a lens and an image pickup device, and these imaging systems are disposed a predetermined base length apart from each other along a horizontal direction. The imaging unit 101 may be configured to have a vertical parallax. In this case, imaging systems have only to be disposed a predetermined base length apart from each other along a vertical direction. FIG. 1 illustrates the imaging unit 101 having the binocular imaging systems. The imaging unit 101 may have trinocular or more imaging systems.

A lens 1011R is a right-eye lens, and collects a light flux from the specimen 30 to a right-eye image pickup device 1012R. A lens 1011L is a left-eye lens, and collects a light flux from the specimen 30 to a left-eye image pickup device 1012L.

The right-eye image pickup device 1012R has a configuration in which a color filter is formed on a light-receiving surface having two-dimensionally arranged pixels comprising photoelectric conversion elements. The right-eye image pickup device 1012R converts the light flux which has entered the light-receiving surface via the lens 1011R to an electric signal (imaging signal) corresponding to the light amount. The left-eye image pickup device 1012L has a configuration similar to that of the right-eye image pickup device 1012R, and converts the light flux which has entered the light-receiving surface via the lens 1011L to an electric signal (imaging signal) corresponding to the light amount. While CCD type and CMOS type image pickup devices are mostly available, any type of image pickup device may be used in the present embodiment.

The image processing unit 102 includes an imaging signal processing unit 1021, a calculating unit 1022, a three-dimensional image processing unit 1023, and an index superimposing unit 1024.

The imaging signal processing unit 1021 includes a right-eye imaging signal processing unit 1021R and a left-eye imaging signal processing unit 1021L. The right-eye imaging signal processing unit 1021R processes the imaging signal input from the right-eye image pickup device 1012R to generate right-eye image data. This processing includes analog processing such as correlated double sampling (CDS) and gain adjustment processing, analog/digital (A/D) processing, and color imaging processing such as color balance correction processing and gray level correction. The left-eye imaging signal processing unit 1021L has a configuration similar to that of the right-eye imaging signal processing unit 1021R, and processes the imaging signal input from the left-eye image pickup device 1012L to generate left-eye image data.

The calculating unit 1022 calculates a region of a three-dimensional reproduction space of the three-dimensional image display 103 in which the three-dimensional image of the specimen is reproduced during three-dimensional display by the three-dimensional image display 103. This calculation corresponds to the measurement of the distance between the imaging unit 101 and each part of the specimen 30. The distance between the imaging unit 101 and each part of the specimen 30 is calculated by a triangular ranging method from, for example, a parallax between the right-eye image data and the left-eye image data. The principle of the triangular ranging method using the binocular imaging systems is briefly described with reference to FIG. 2. When the specimen 30 is imaged by the use of the binocular imaging systems, light from a certain part of the specimen 30 enters a pixel located x1 apart from the reference position in the right-eye image pickup device 1012R, while the light enters a pixel located x2 apart from the reference position in the left-eye image pickup device 1012L. The following relation is known to be satisfied:

$$L = B \times f/(x1+x2) \tag{1}$$

wherein B is a base length between the binocular imaging systems, f is the focal distance of the lens, and L is the distance from the lens to the specimen 30. In accordance with (Expression 1), the distance L to the specimen in any pixel can be figured out by the detection of the parallax (x1+x2). The parallax (x1+x2) can be detected by, for example, a block matching method. The block matching method is a method of detecting a particular block (a block including the specimen 30) of the left-eye image data and a block having the highest correlation (e.g., a block having the minimum difference absolute value) from the right-eye image data. In this instance, the positional difference between the block of the right-eye image data and the block of the left-eye image data is the parallax (x1+x2). It is also possible to obtain distance information pixel by pixel by performing the calculation shown in (Expression 1) for each pixel.

The three-dimensional image processing unit 1023 controls the three-dimensional display operation in the three-dimensional image display 103. For example, a lenticular lens method can be used as a method of the three-dimensional display. According to the lenticular lens method, a lenticular lens having cylindrical lenses is formed on the display surface of the three-dimensional image display 103, and a right-eye image and a left-eye image displayed on the three-dimensional image display 103 are respectively brought into the right eye and left eye of an observer by the lenticular lens to provide a stereoscopic view to the observer. It should be appreciated that the use of the lenticular lens method as the method of the three-dimensional display is not necessary. The present embodiment is applicable to various three-dimensional display methods; for example, a liquid crystal lens is used instead of the lenticular lens, or a naked-eye parallel method is used.

The index superimposing unit 1024 superimposes an annotation image (e.g., a virtual arrow image) on the three-dimensional image of the specimen 30 during the three-dimensional image display by the three-dimensional image processing unit 1023 on the basis of the information on the distance to the specimen 30 obtained in the calculating unit 1022 and operational information from the PC 20. Data of various annotation images are stored in the index superimposing unit 1024 for annotation image superimposition.

The three-dimensional image display 103 is, for example, a liquid crystal display device having the lenticular lens formed on its display surface, and performs three-dimensional display in response to the input of the right-eye image data and the left-eye image data from the three-dimensional image processing unit 1023.

The operation unit 104 is the operation unit of the medical three-dimensional observation apparatus 10. The operation unit 104 is operated by the observer, and issues an instruction to move a virtual arrow image 40 in a display screen of the three-dimensional image display 103. The operation unit 104 is a pointing device such as a mouse.

The PC 20 roughly includes a controller 201, an image display 202, and an operation unit 203.

The controller 201 is, for example, a CPU. The controller 201 receives the left-eye image data from the left-eye imaging signal processing unit 1021L, and controls to display a two-dimensional image corresponding to the received image data on the image display 202. The controller 201 inputs information on the operation by the operation unit 203 to the index superimposing unit 1024.

The image display 202 is, for example, a liquid crystal display device, and performs two-dimensional display in response to the input of the left-eye image data from the controller 201. The image display 202 may be a display device capable of three-dimensional display.

The operation unit 203 is operated by the observer, and issues an instruction to move the virtual arrow image 40 in the display screen of the image display 202. The operation unit 203 is a pointing device such as a mouse.

The operation of the medical three-dimensional observation apparatus 10 shown in FIG. 1 is described below. When the medical three-dimensional observation apparatus 10 is activated by the observer, the specimen 30 is imaged by the imaging unit 101. An imaging signal obtained by the right-eye imaging system of the imaging unit 101 is processed by the right-eye imaging signal processing unit 1021R. An imaging signal obtained by the left-eye imaging system of the imaging unit 101 is processed by the left-eye imaging signal processing unit 1021L.

The right-eye image data obtained by the right-eye imaging signal processing unit 1021R and the left-eye image data obtained by the left-eye imaging signal processing unit 1021L are input to the calculating unit 1022. The calculating unit 1022 calculates the distance to the specimen 30 pixel by pixel from a parallax between the right-eye image data and the left-eye image data. The pixel-by-pixel distance information and parallax information are retained in the calculating unit 1022.

The right-eye image data obtained by the right-eye imaging signal processing unit 1021R and the left-eye image data obtained by the left-eye imaging signal processing unit 1021L are also input to the three-dimensional image processing unit 1023. The three-dimensional image processing unit 1023 controls the display operation of the three-dimensional image display 103 so that the right-eye image corresponding to the right-eye image data is displayed in the right-eye display pixels of the three-dimensional image display 103 and so that the left-eye image corresponding to the left-eye image data is displayed in the left-eye display pixels of the three-dimensional image display 103.

The index superimposing unit 1024 superimposes a virtual arrow image as an annotation image synchronously with the three-dimensional display operation of the three-dimensional image processing unit 1023. An example of the superimposition of an arrow image is described. Various annotation images other than the arrow image may be superimposed.

At the time of the activation of the medical three-dimensional observation apparatus 10, the virtual arrow image is displayed at a fixed position (e.g., a central position) of the three-dimensional image display 103. The parallax (x1+x2) that conforms to the distance L in the part of the specimen corresponding to the end position of the virtual arrow image is given to the annotation images to be superimposed so that the right-eye image data and the left-eye image data so that the annotation images will be superimposed with the same depth as a specimen image displayed on the three-dimensional image display 103 as a three-dimensional image.

The observer operates the operation unit 104 while watching the three-dimensional image displayed on the three-dimensional image display 103 or operates the operation unit 203 while watching the two-dimensional image displayed on the image display 202, and thereby issues an instruction to move the display position of the virtual arrow image. In response to this operation, the index superimposing unit 1024 acquires, from the calculating unit 1022, distance information L of the pixels at a position (X, Y) on the display screen specified by the operation unit 104 or the operation unit 203. This position (X, Y) is, for example, a position on the left-eye image data.

After acquiring the distance information L, the index superimposing unit 1024 changes the parallax of the virtual arrow image 40 so that the virtual arrow image 40 is displayed at the depth corresponding to the acquired distance information L. When the position of the virtual arrow image 40 is changed to the position (X, Y) on the left-eye image data, the virtual arrow image 40 is superimposed on a right-eye image R so that the parallax between the virtual arrow image 40 in the right-eye image R and the virtual arrow image 40 in a left-eye image L will be (x1+x2) as shown in FIG. 3.

Figure 4:
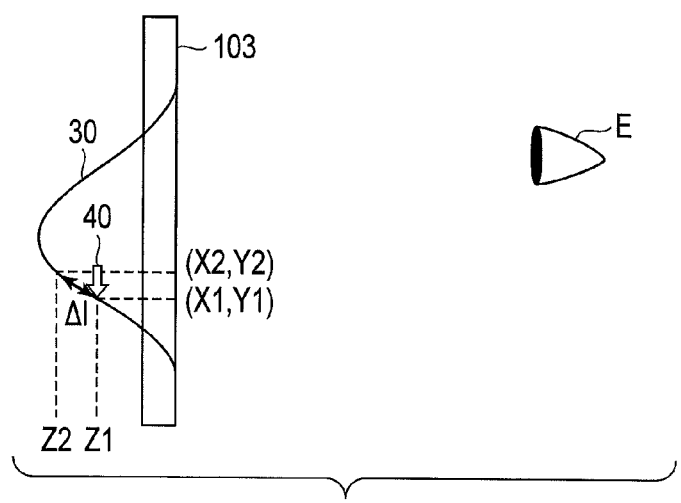
FIG. 4 is a diagram showing the relation between the operation amount of an operation unit and the displacement amount of the display position of the virtual arrow image.

As described above, according to the present embodiment, the parallax is given to the virtual arrow image 40 to be superimposed on the three-dimensional image in accordance with the actual distance of the position of the specimen 30 specified on the three-dimensional image display 103 by the observer. Thus, as shown in FIG. 4, it appears to an eye E of the observer that the virtual arrow image 40 is added to the specimen in the intended three-dimensional image with the same depth.

[Modification]

A modification of the present embodiment is described below. In the example described above, the virtual arrow image 40 is superimposed on the right-eye image data R and the left-eye image data L to give the parallax. Actually, when superimposing the virtual arrow image 40, it is preferable to superimpose the virtual arrow image 40 without hiding the image of the specimen 30. To this end, when the position (X, Y) is specified, the distance of the specified position (X, Y) is compared with the distance of its periphery, and if the image of the specimen 30 is located closer to the periphery of the virtual arrow image than the virtual arrow image, the virtual arrow image 40 is superimposed to avoid the image of the specimen 30 at a near point. This prevents unnatural display of the virtual arrow image 40 buried in the image of the specimen 30 when the virtual arrow image 40 is displayed.

In the sense of the improvement in operational feeling, it is preferable that the change amount of the display position of the virtual arrow image 40 is linear relative to the operation amount of the operation unit 104 or the operation unit 203. The pixel-by-pixel distance L is known. Therefore, a display position (X, Y, Z) in the three-dimensional image of the virtual arrow image 40 is determined so that a change amount $\Delta l$ of the display position of the virtual arrow image 40 relative to an operation amount $\Delta M$ (X, Y) shown in FIG. 4 will be constant. Here, it is preferable that the movement amount $\Delta l$ is constant relative to the change in which the movement amount including the movement amount in the depth direction is $\Delta M$.

Figure 5:
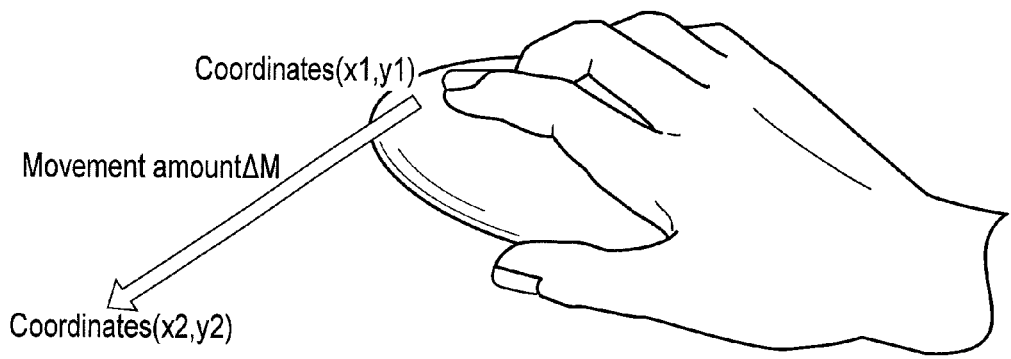
FIG. 5 is a diagram illustrating an operation amount $\Delta M$.
Figure 6:
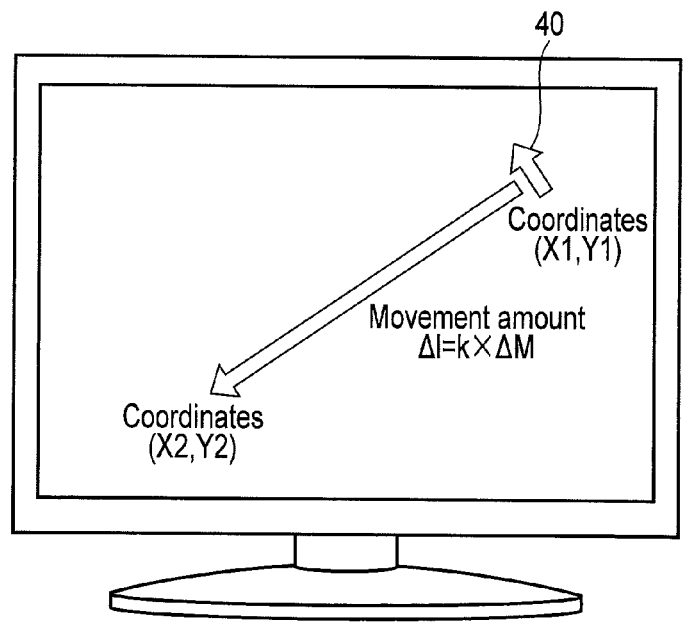
FIG. 6 is a diagram illustrating a movement amount $\Delta l$ in which the virtual arrow image is simply moved on a two-dimensional image.

For example, an operation amount in which the observer has moved the operation unit 203 (mouse) from coordinates (x1, y1) to coordinates (x2, y2) as shown in FIG. 5 is $\Delta M$. In response to the operation amount $\Delta M$, the virtual arrow image 40 is moved on the two-dimensional image from coordinates (X1, Y1) to coordinates (X2, Y2) as shown in FIG. 6. A movement amount Δl in this case is represented by the following expression:

$$\Delta l = k \times \Delta M (k \text{ is a predetermined coefficient}).$$

In the case of control in which the movement amount in the depth direction is not included as in the above expression, the virtual arrow image 40 moves on the three-dimensional image display 103 at intervals indicated by the arrows A in FIG. 7. As obvious from FIG. 7, the movement of the virtual arrow image per unit time is faster in the depth direction, so that the observer cannot perform fine pointing at the image position where depth changes. To perform fine pointing even at the image position where depth changes, it is necessary to move the virtual arrow image 40 as shown in FIG. 8. The distance between two points in the slope in FIG. 8 is represented by the following expression:

$$\sqrt{((X1-X2)^2+(Y1-Y2)^2+(Z1-Z2)^2)}$$

wherein X1, Y1, and Z1 respectively represent horizontal coordinates, vertical coordinates, and depth coordinates of the virtual arrow image 40 before movement, and X2, Y2, and Z2 respectively represent horizontal coordinates, vertical coordinates, and depth coordinates of the virtual arrow image 40 after movement. If X2, Y2, and Z2 are determined so that the above expression will be Δl, the virtual arrow image can be finely operated even in the case of a subject which changes in the depth direction. The operation amount of the operation unit 104 or the operation unit 203 are matched to the displacement amount of the virtual arrow image 40 in the three-dimensional image as described above, so that it is possible to smoothly provide an annotation to a desired position in the three-dimensional image. Although the operation amount of the operation unit 104 or the operation unit 203 are matched to the displacement amount of the virtual arrow image 40 in the present modification here, the movement velocity of the operation unit 104 or the operation unit 203 may be matched to the displacement amount of the virtual arrow image 40.

While it is possible to adjust the reproduction depth of the specimen 30 in the display 103 by shifting the right-eye image and the left-eye image in the horizontal direction in the three-dimensional image processing unit 1023, the virtual arrow image also includes giving a parallax to which its shift amount is added.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical three-dimensional observation apparatus comprising:
   an imaging unit comprising a first imaging system and a second imaging system for an observation of a three-dimensional image, the first imaging system including a first observation window and generating a left image signal, and the second imaging system including a second observation window and generating a right image signal;
   an instruction unit operated by an observer, configured to issue an instruction to move an annotation image for the three-dimensional image as a two-dimensional position information;
   a calculating unit configured to calculate a depth position of the annotation image for the three-dimensional image corresponding to a position indicated by the two-dimensional position information on the basis of a distance between an optical axis of the first imaging system and an optical axis of the second imaging system;
   a three-dimensional image processing unit configured to generate a left image and a right image for the observation of a three-dimensional image on the basis of the left image signal and the right image signal;
   an index superimposing unit configured to calculate a display position of the annotation image for the three-dimensional image on the basis of the depth position calculated by the calculating unit and the two-dimensional position information issued by the instruction unit, and to superimpose the annotation image on each of the left image and the right image on the basis of the display position; and
   a display configured to display the left image and the right image superimposed the annotation image so that the observation of the three-dimensional image is able to be performed,
   wherein the index superimposing unit compares a distance corresponding to the depth position with a distance corresponding to a periphery of the position indicated by the two-dimensional position information, so that the display position of the annotation image is always located before an image of a specimen in the left image and the right image, and superimposes the annotation image on each of the left image and the right image to avoid the image of a specimen if the image of the specimen is located closer to the periphery of the annotation image than the annotation image.

* * * * *